United States Patent
Gunn et al.

(10) Patent No.: US 11,278,423 B2
(45) Date of Patent: Mar. 22, 2022

(54) EXPANDABLE INTERBODY DEVICES

(71) Applicant: MiRus LLC, Atlanta, GA (US)

(72) Inventors: Josh Gunn, Atlanta, GA (US); Jay Yadav, Sandy Springs, GA (US); Wayne Gray, Atlanta, GA (US); Noah Roth, Atlanta, GA (US); Adam Marrocco, Kennesaw, GA (US)

(73) Assignee: MiRus LLC, Marietta, GA (US)

( * ) Notice: Subject to any disclaimer, the term of this patent is extended or adjusted under 35 U.S.C. 154(b) by 250 days.

(21) Appl. No.: 16/147,986

(22) Filed: Oct. 1, 2018

(65) Prior Publication Data

US 2019/0133784 A1    May 9, 2019

Related U.S. Application Data

(60) Provisional application No. 62/565,336, filed on Sep. 29, 2017.

(51) Int. Cl.
*A61F 2/44* (2006.01)
*A61B 17/70* (2006.01)
(Continued)

(52) U.S. Cl.
CPC ............ *A61F 2/4455* (2013.01); *A61B 17/70* (2013.01); *A61F 2/4611* (2013.01);
(Continued)

(58) Field of Classification Search
None
See application file for complete search history.

(56) References Cited

U.S. PATENT DOCUMENTS 6,126,689 A    10/2000  Brett
6,443,989 B1   9/2002   Jackson
(Continued)

FOREIGN PATENT DOCUMENTS

WO    2018/053403    3/2018

OTHER PUBLICATIONS

Globus Medical, RISE, titanium expandable lumbar fusion device, available at www.globusmedical.com/portfolio/rise/, last accessed May 20, 2019, 3 pages.
(Continued)

*Primary Examiner* — Sameh R Boles
(74) *Attorney, Agent, or Firm* — Ulmer & Berne LLP; Brian Turung

(57) ABSTRACT

An example expandable interbody device can include a structural body having an upper endplate and a lower endplate, where the endplates are shaped to nest tightly in a closed position. The device can include at least one wedge block and at least one linkage block arranged between the upper and lower endplates of the structural body. The device can include a drive screw threaded through the at least one wedge block and the at least one linkage block. The drive screw can be configured to rotate and drive the at least one wedge block to expand the upper and lower endplates of the structural body from the closed position to an intermediate position. Additionally, the drive screw can be further configured to rotate and drive the at least one linkage block to expand the upper and lower endplates of the structural body from the intermediate position to an open position.

12 Claims, 13 Drawing Sheets

(51) Int. Cl.
    *A61F 2/46*     (2006.01)
    *A61F 2/30*     (2006.01)

(52) U.S. Cl.
    CPC ........... *A61F 2/30771* (2013.01); *A61F 2/442* (2013.01); *A61F 2002/30484* (2013.01); *A61F 2002/30507* (2013.01); *A61F 2002/30556* (2013.01); *A61F 2002/30579* (2013.01)

(56) References Cited

U.S. PATENT DOCUMENTS

| | | | |
|---|---|---|---|
| 6,773,460 B2 | 8/2004 | Jackson | |
| 6,849,093 B2 | 2/2005 | Michelson | |
| 7,128,760 B2 | 10/2006 | Michelson | |
| 7,731,751 B2 | 6/2010 | Butler et al. | |
| 7,763,028 B2 | 7/2010 | Lim et al. | |
| 7,828,849 B2 | 11/2010 | Lim | |
| 7,951,199 B2 | 5/2011 | Miller | |
| 8,043,381 B2 | 10/2011 | Hestad et al. | |
| 8,105,382 B2 | 1/2012 | Olmos et al. | |
| 8,486,149 B2 | 7/2013 | Saidha et al. | |
| 8,491,659 B2 | 7/2013 | Weiman | |
| 8,523,944 B2 | 9/2013 | Jimenez et al. | |
| 8,574,300 B2 | 11/2013 | McManus et al. | |
| 8,628,577 B1 | 1/2014 | Jimenez | |
| 8,628,578 B2 | 1/2014 | Miller et al. | |
| 8,632,593 B2 | 1/2014 | Suh et al. | |
| 8,715,351 B1 | 5/2014 | Pinto | |
| 8,795,366 B2 | 8/2014 | Varela | |
| 8,845,731 B2 | 9/2014 | Weiman | |
| 8,852,279 B2 | 10/2014 | Weiman | |
| 8,888,854 B2 | 11/2014 | Glerum et al. | |
| 8,894,711 B2 | 11/2014 | Varela | |
| 8,940,049 B1 | 1/2015 | Jimenez et al. | |
| 9,034,041 B2 | 5/2015 | Wolters et al. | |
| 9,186,258 B2 | 11/2015 | Davenport et al. | |
| 9,198,772 B2 | 12/2015 | Weiman | |
| 9,233,007 B2 | 1/2016 | Sungarian et al. | |
| 9,278,008 B2 | 3/2016 | Perloff et al. | |
| 9,393,130 B2 | 7/2016 | Suddaby et al. | |
| 9,445,919 B2 | 9/2016 | Palmatier et al. | |
| 9,549,824 B2 | 1/2017 | McAfee | |
| 9,554,918 B2 | 1/2017 | Weiman | |
| 9,561,116 B2 | 2/2017 | Weiman et al. | |
| 9,867,717 B2 | 1/2018 | Jimenez | |
| 9,913,727 B2 | 3/2018 | Thommen | |
| 9,924,972 B2 | 3/2018 | Yue | |
| 2013/0190876 A1 | 7/2013 | Drochner et al. | |
| 2014/0336764 A1* | 11/2014 | Masson | A61F 2/4455 623/17.15 |
| 2015/0272743 A1* | 10/2015 | Jimenez | A61F 2/447 623/17.16 |
| 2016/0051384 A1 | 2/2016 | Patel | |
| 2016/0166396 A1 | 6/2016 | McClintock | |
| 2017/0112630 A1 | 4/2017 | Kuyler et al. | |
| 2017/0224505 A1 | 8/2017 | Butler et al. | |
| 2017/0281361 A1 | 10/2017 | Jimenez et al. | |
| 2017/0367842 A1 | 12/2017 | Predick et al. | |
| 2019/0008995 A1 | 1/2019 | Roth | |
| 2019/0133784 A1 | 5/2019 | Gunn et al. | |

OTHER PUBLICATIONS

K2M Complex Spine Innovations, MOJAVE™ PL 3D Expandable Interbody System—K2M, available at https://www.k2m.com/products/product/mojave-pl-3d/, last accessed May 20, 2019, 1 page.

K2M Complex Spine Innovations, K2M Announces US Launch of First-to-Market 3D-Printed Expandable Interbody MOJAVE™ PL 3D Expandable Featuring Lamellar 3D Titanium Technology™, May 16, 2018, 2 pages.

Non-Final Office Action in connection to U.S. Appl. No. 16/422,200, dated Feb. 1, 2021.

\* cited by examiner

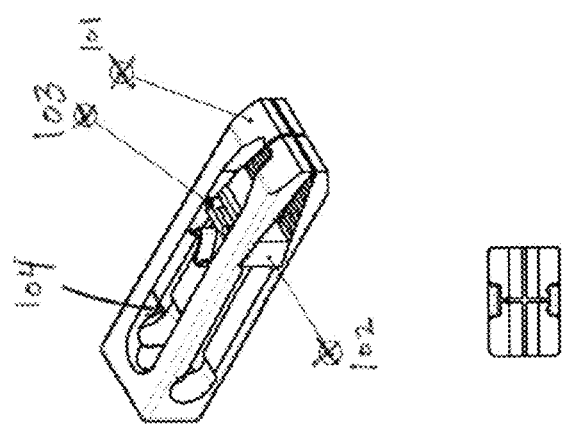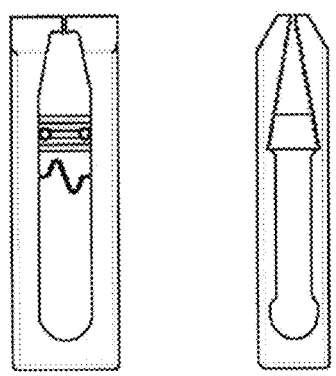
FIG. 2

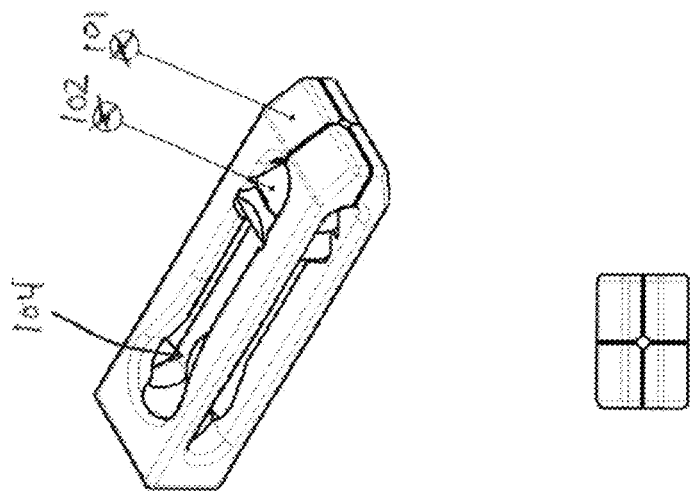
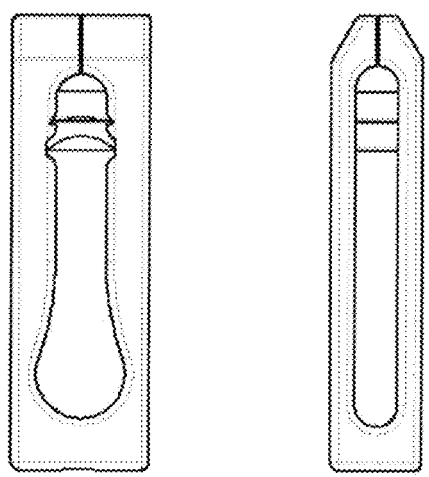
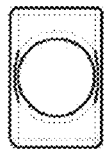
FIG. 3

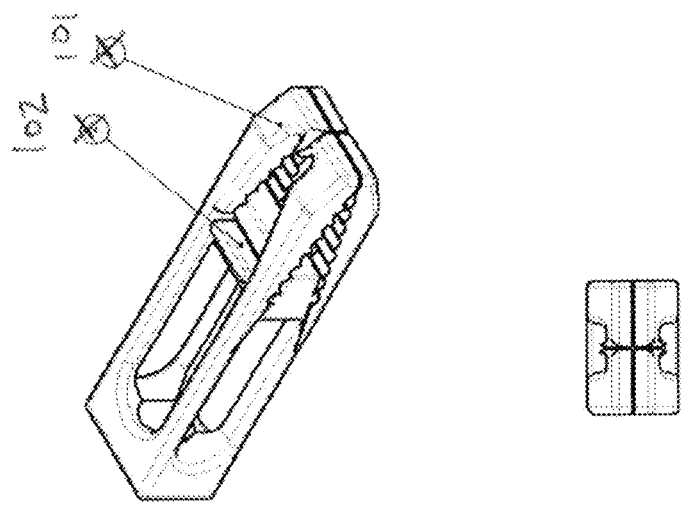
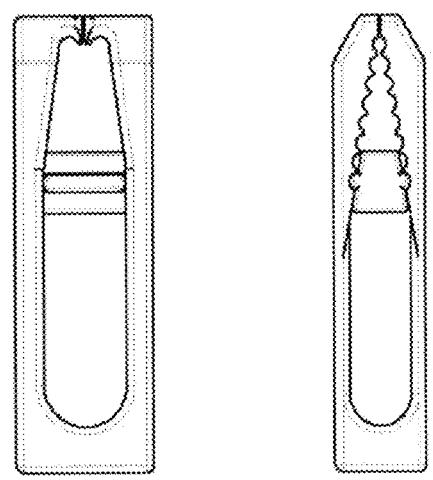
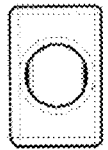
FIG. 4

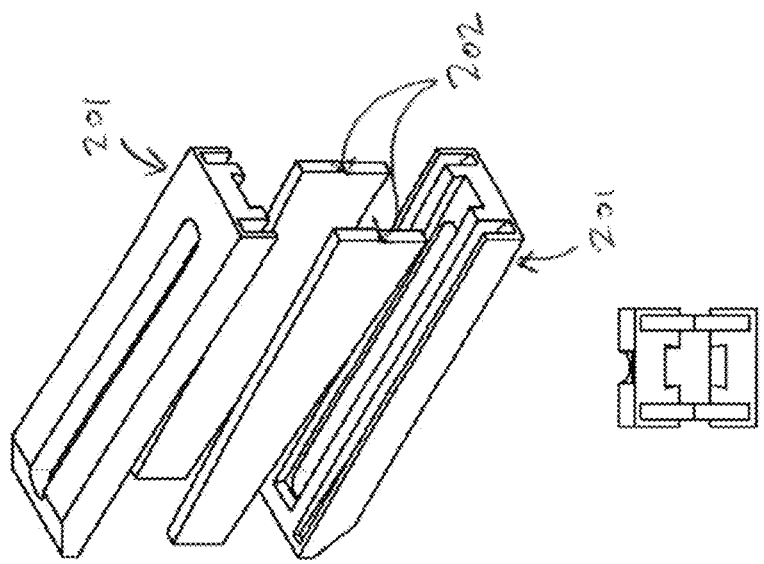
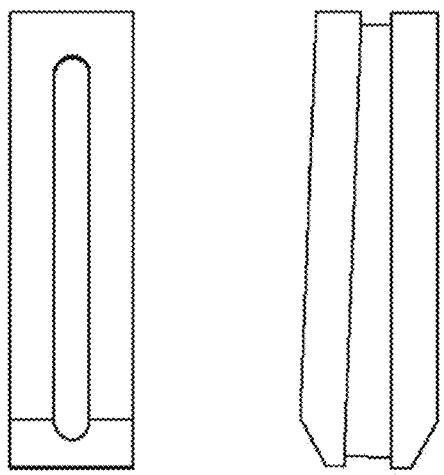
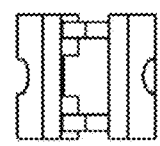
FIG. 5

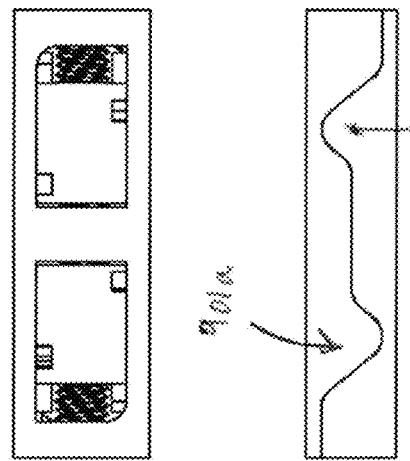
FIG. 9
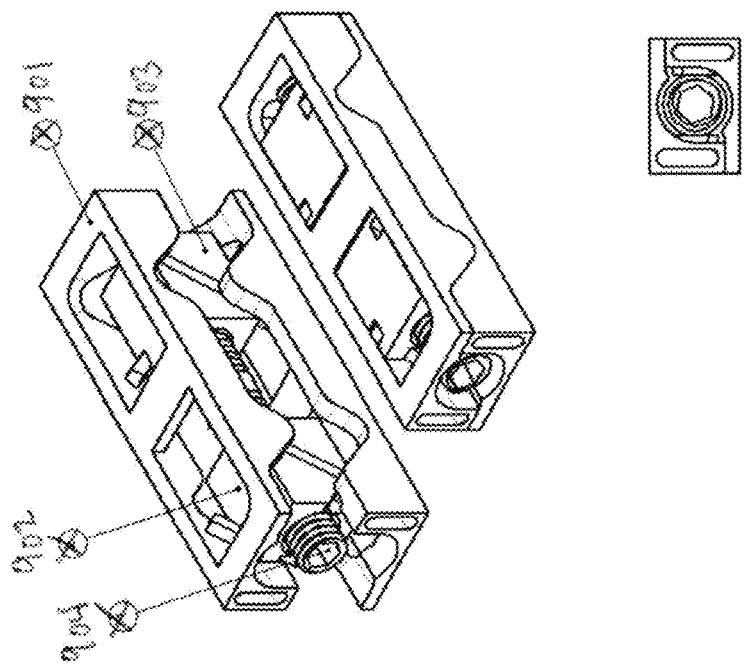

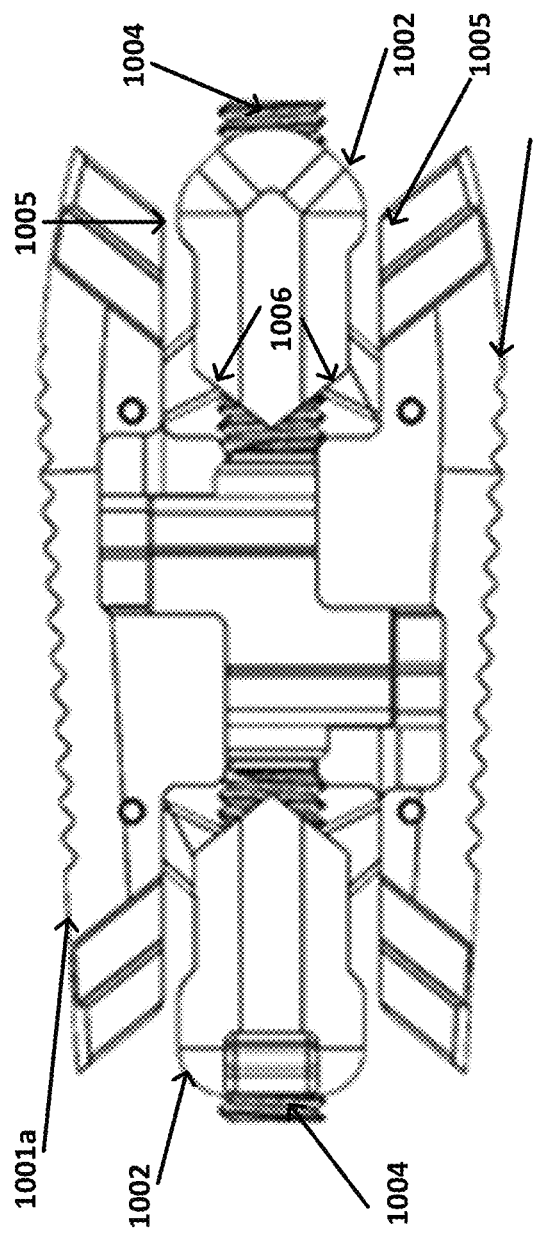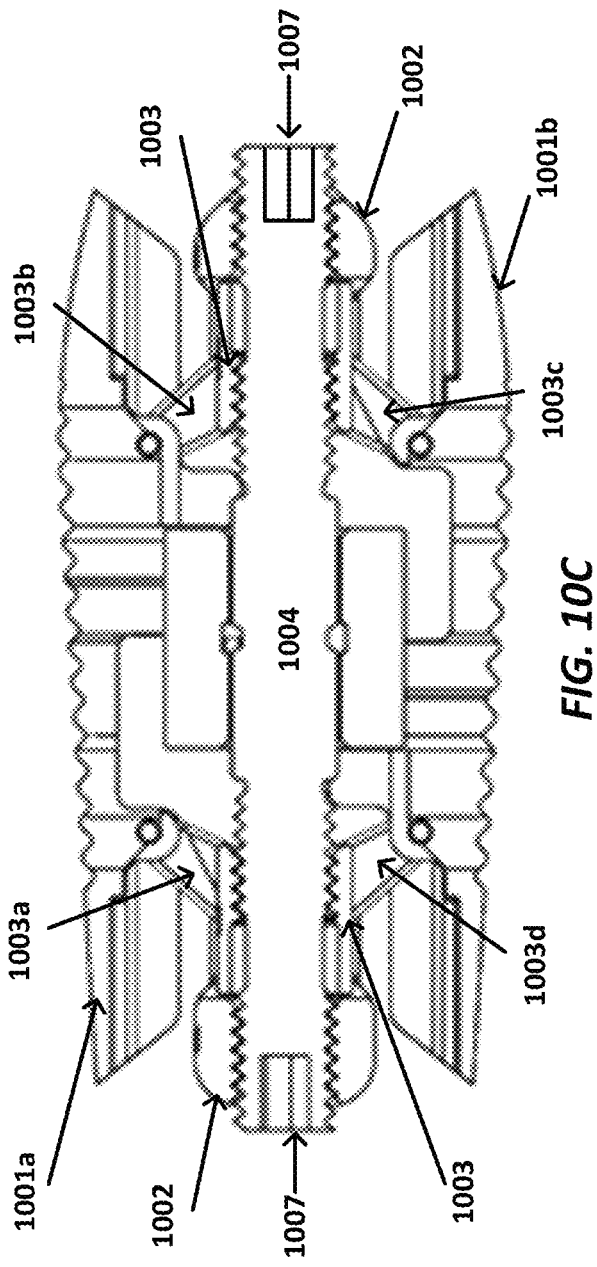

EXPANDABLE INTERBODY DEVICES

CROSS-REFERENCE TO RELATED APPLICATIONS

This application claims the benefit of U.S. provisional patent application No. 62/565,336, filed on Sep. 29, 2017, and entitled "Expandable Interbody Devices," the disclosure of which is expressly incorporated herein by reference in its entirety.

BACKGROUND

An interbody device is a prosthesis used during spinal surgery. An interbody device is inserted into the space between spinal disks to provide stability. For example, an interbody device can be introduced between vertebrae of a patient's spine (e.g., in the disk space between adjacent vertebrae) for fixation with bone to immobilize the joint as part of a surgical treatment.

SUMMARY

Expandable interbody devices are described herein. In one implementation, an expandable interbody device has a dual stage mechanism (e.g., wedge and linkage blocks) controlled by rotation of a drive screw. The threads of the drive screw are timed such that only the wedge blocks are engaged by the drive screw in a first stage. Angled grooves of the wedge blocks engage with angled bosses on the endplates of the expandable interbody device, which causes the device to expand. Then, in a second stage, the threads of the drive screw engage the linkage blocks. Additionally, in the second stage, angled bosses on the endplates of the expandable interbody device disengage from the wedge blocks, which allows the linkage blocks to control expansion of the device.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 2 illustrates an expandable interbody device according to another implementation described herein.

FIG. 3 illustrates an expandable interbody device according to another implementation described herein.

FIG. 4 illustrates an expandable interbody device according to another implementation described herein.

FIG. 5 illustrates an expandable interbody device according to another implementation described herein.

FIG. 9 illustrates an expandable interbody device according to another implementation described herein.

FIG. 10A-10H illustrate an expandable interbody device according to another implementation described herein. FIG. 10A illustrates a side view of the expandable interbody device during a first (e.g., initial) stage of expansion. FIG. 10B illustrates a side view of the expandable interbody device during a second stage of expansion. FIG. 10C illustrates a cross-sectional view of the expandable interbody device during the second stage of expansion. FIG. 10D illustrates an end view of the expandable interbody device. FIG. 10E illustrates a perspective view of the expandable interbody device in a closed position. FIG. 10F illustrates a perspective view of the expandable interbody device in an open position. FIG. 10G illustrates a side view of the expandable interbody device in a closed position. FIG. 10H illustrates a side view of the expandable interbody device in an open position.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Figure 1:
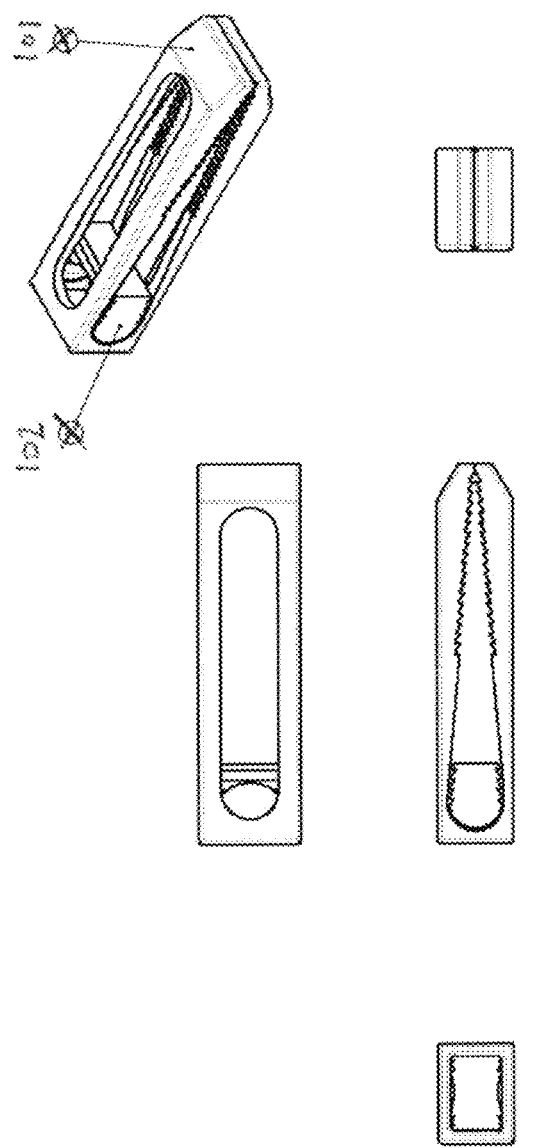
FIG. 1 illustrates an expandable interbody device according to an implementation described herein.

Referring now to FIG. 1, upon translation of sliding ramp 102, upper and lower halves of the main structural body 101 will be forced apart thus providing expansion of the interbody device. The ratcheting teeth on the ramp and main body will prevent the ramp from reversing and the device collapsing under load.

Referring now to FIG. 2, upon translation of sliding ramp 102, upper and lower halves of the main structural body 101 will be forced apart thus providing expansion of the interbody device. The ratcheting teeth on the ramp and main body will prevent the ramp from reversing and the device collapsing under load. Additionally, the main body is split to allow lateral expansion. As the sliding ramp traverses a channel 104 of the structural body, the pins 103 will ride along the ramped surface on the inside of the graft opening to expand laterally while the main ramp surfaces expand in height.

Referring now to FIG. 3, upon translation of sliding ramp 102, upper and lower halves of the main structural body 101 will be forced apart thus providing expansion of the interbody device. The ratcheting teeth on the ramp and main body will prevent the ramp from reversing and the device collapsing under load. As the sliding ramp traverses a channel 104 of the structural body, the cones-shaped ramp interface will apply expansion force radially generating width and height expansion.

Referring now to FIG. 4, the device operates similarly to the device shown in FIG. 2 with main structural body 101 and sliding ramp 102. In FIG. 4, the teeth have been changed from traditional ratchet teeth to partial cylinders to maintain good contact as the contact angle changes with expansion.

Referring now to FIG. 5, both top and bottom endplates 201 load onto inserter which utilizes the center dovetail groove to retain them. The endplates are inserted into the disc space and expanded via the inserter, and then the sidewalls 202 are delivered (guided by the attached inserter) into the side grooves. The sidewalls could either taper-lock, snap-lock, or lock with a cam/cover mechanism to retain them. The inner inserter mechanism can then be removed and the device post-packed with graft.

Figure 6:
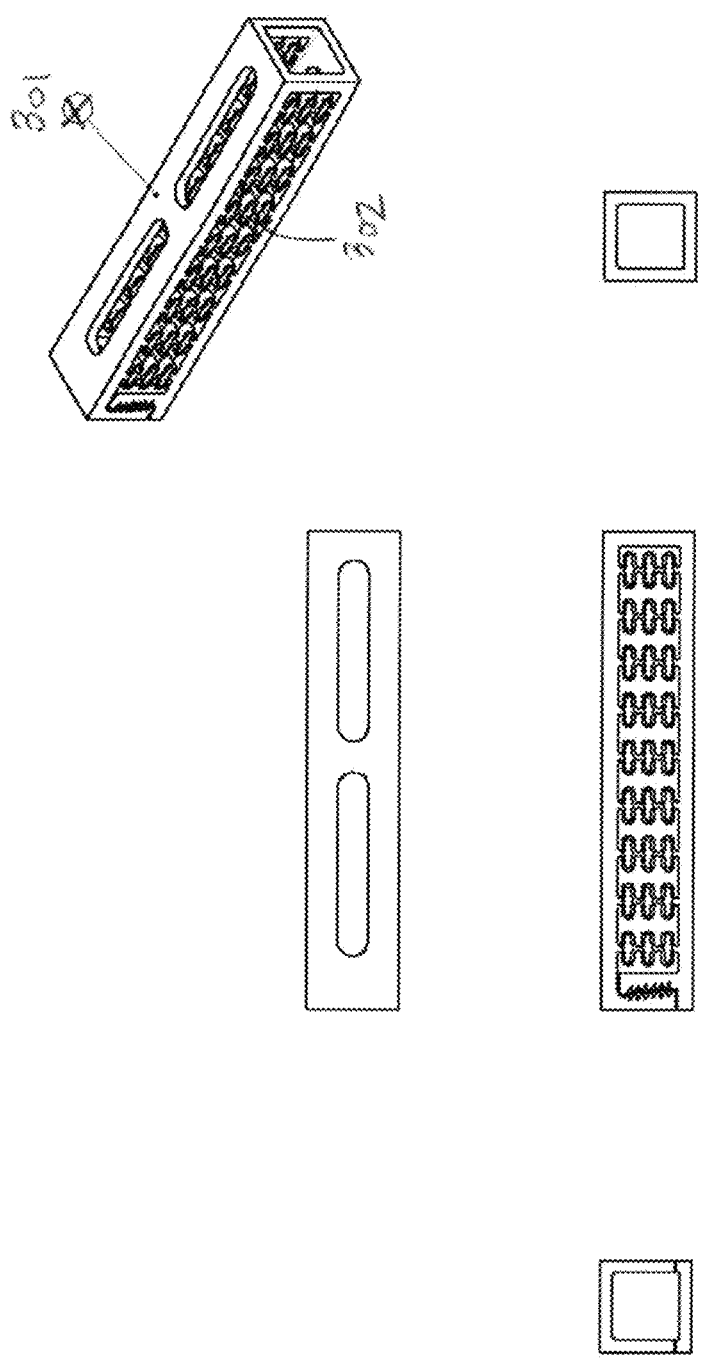
FIG. 6 illustrates an expandable interbody device according to another implementation described herein.

Referring now to FIG. 6, many repeating stent-like cutout structures 302 allow the device 301 to be forcibly expanded in height (and possibly adapted to width as well). Said expansion will permanently deform the support structures and the device will maintain its expanded shape. Further support can be added by means of the ratchet mechanism, which as the device expands, will engage spring-loaded ratchet teeth to provide post-expansion compression support.

Figure 7:
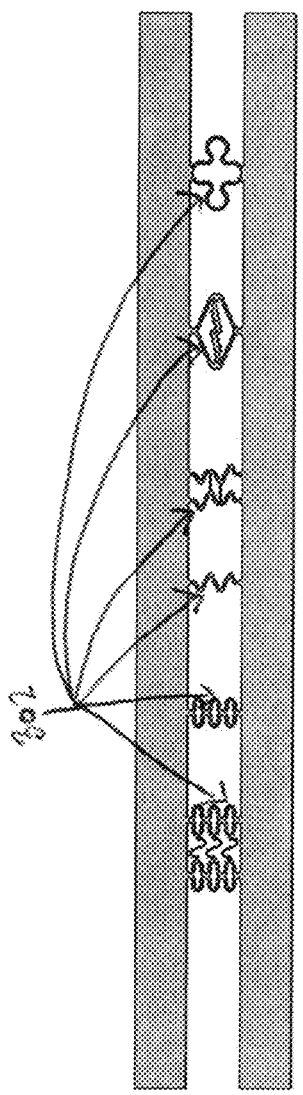
FIG. 7 illustrates an expandable interbody device according to another implementation described herein.

Referring now to FIG. 7, examples of many types of stent structures 302 that could be adapted to concept shown in FIG. 6. Of particular note is second from the last, which has an integral ratchet in the stent-like support structure. This would engage the ratchet teeth as the stent is expanded and the ratchet teeth are drawn forcibly together. The engaged teeth would then provide additional resistance to the structure collapsing under compressive loads.

Figure 8:
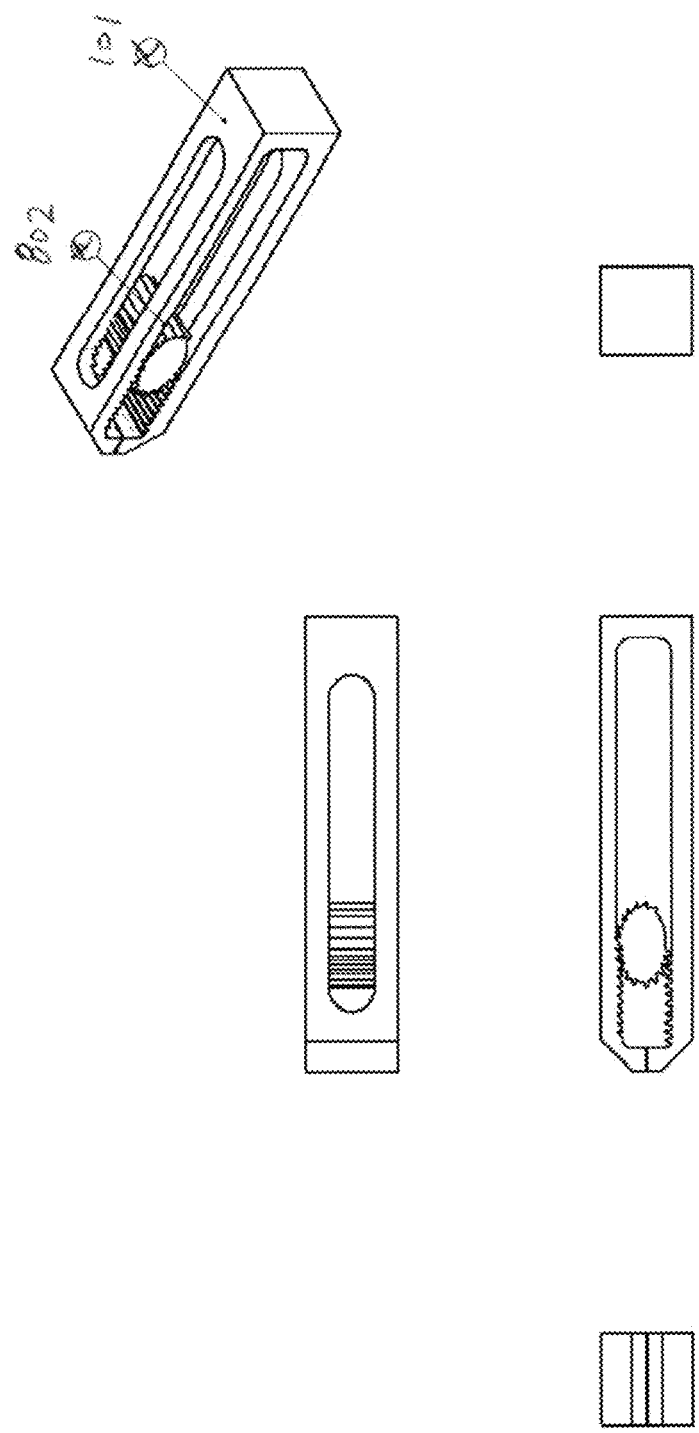
FIG. 8 illustrates an expandable interbody device according to another implementation described herein.

Referring now to FIG. 8, as the elongate support member 802 is translated distally, the gear rack engages thus forcing the motion to become rotational and translational (rolling as it traverses the gear rack). As the elongate member rotates, the point-to-point distance spanning the top and bottom portions of the main body 101 elongates towards the maximum height achievable (equal to the length of the longest axis of the elongate member plus the thickness of top and bottom portions of the main body). As the elongate member traverses the main body, the top row of ratchet teeth engage the main body. These teeth resist the elongate member traversing in reverse and collapsing under compressive loads.

Referring now to FIG. 9, top and bottom endplate 901 are the same component. They are designed to nest tightly with protrusions 901a, 901b beyond center line to allow the ramp bosses to extend farther and thus allow more expansion. These are support structures with angled grooves to accept ramped bosses inside of the endplates. Sliding ramp support bodies 902, 903 are threaded in opposite-handed directions so that as the drive screw is rotated the motion of the two sliding ramps are opposed. As the drive screw 904 is rotated the sliding ramps are forced apart. The engaged ramped bosses and grooves in the endplates and ramps will wedge the endplates apart in a parallel expansion motion.

Referring now to FIGS. 10A-10H, an expandable interbody device is shown. The device can include a structural body having an upper endplate 1001a and a lower endplate 1001b (collectively "endplates 1001"), where the upper and lower endplates 1001 are shaped to nest tightly in a closed position. The endplates 1001 are configured to make direct contact with the patient's bone, e.g., with vertebral bodies in the section of the spine undergoing fixation/fusion. The endplates 1001 are designed to nest tightly with protrusions beyond center line to allow angled bosses (e.g., angled bosses 1005) to extend farther and thus allow more expansion of the structural body. The device can also include at least one wedge block 1002 arranged between the upper and lower endplates 1001 of the structural body, and at least one linkage block 1003 arranged between the upper and lower endplates 1001 of the structural body. The wedge blocks 1002 are support structures with angled grooves (e.g., angled grooves 1006) designed to accommodate angled bosses on the outside of the endplates 1001. The linkage blocks 1003 are support structures that attach to one or more linkages 1003a-1003d (e.g., levers). The device can further include a drive screw 1004 threaded through the at least one wedge block 1002 and the at least one linkage block 1003.

As shown in FIGS. 10A-10H, the device includes a plurality of wedge blocks 1002 arranged between the upper and lower endplates 1001 and on opposite sides of the structural body (e.g., proximal and distal wedge blocks). Each of the wedge blocks 1002 can be threaded in an opposite-handed direction such that the drive screw 1004 is configured to rotate and drive the wedge blocks 1002 in opposite directions and towards the center of the device. Additionally, as shown in FIGS. 10A-10H, the device can further include a plurality of linkage blocks 1003 arranged between the upper and lower endplates 1001 and on opposite sides of the structural body. In some implementations, the device can optionally include eight linkages. For example, the device can include two linkages per articular point, e.g., four linkages on each side of the device for a total of eight. It should be understood that the number of linkages is provided only as an example. Each of the linkage blocks 1003 can be threaded in an opposite-handed direction such that the drive screw 1004 is configured to rotate and drive the linkage blocks 1003 in opposite directions.

Figure 10A:
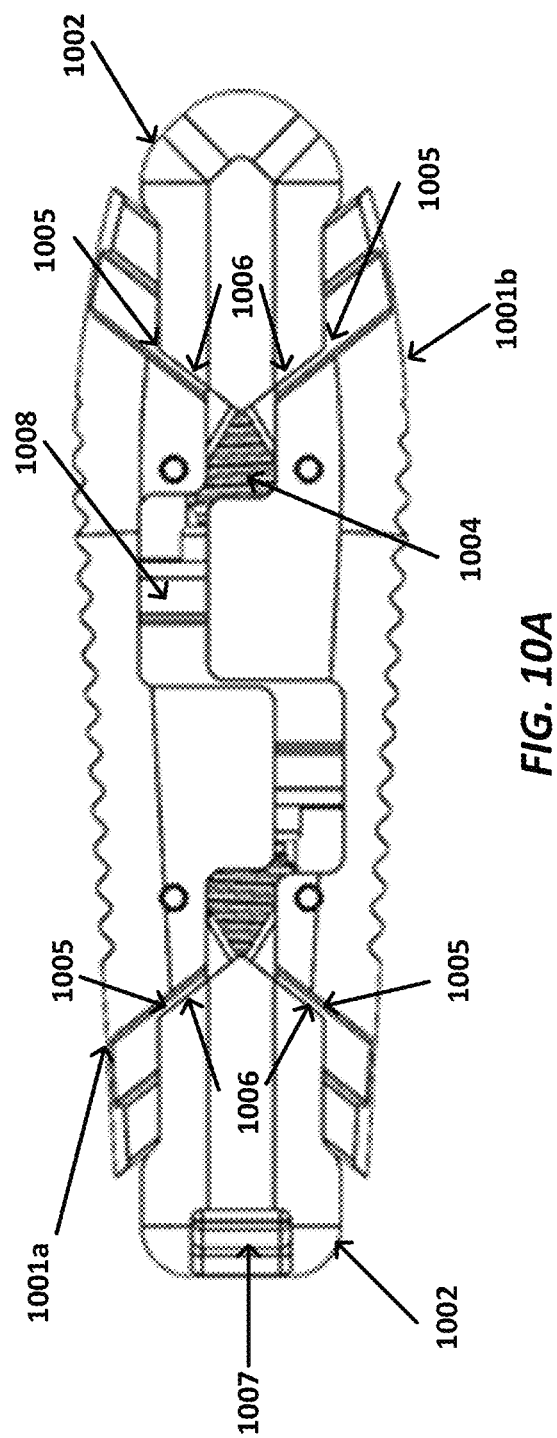
Figure 10D:
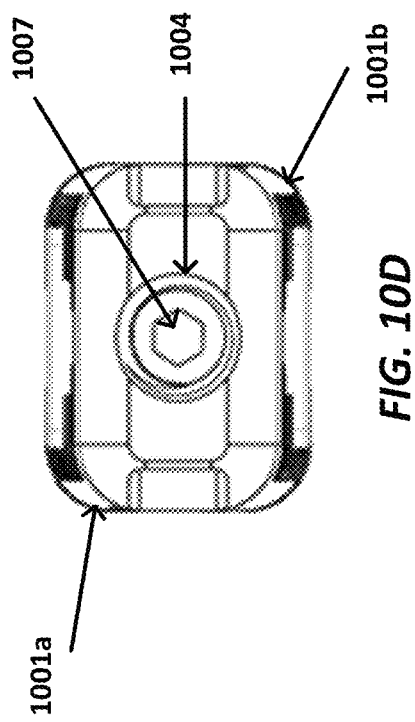
Figure 10F:
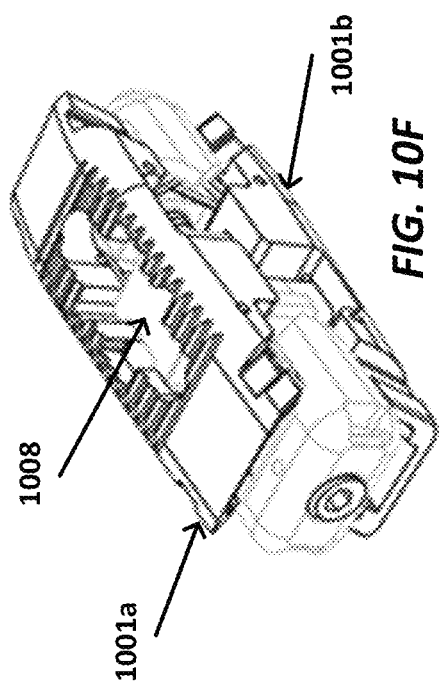
Figure 10E:
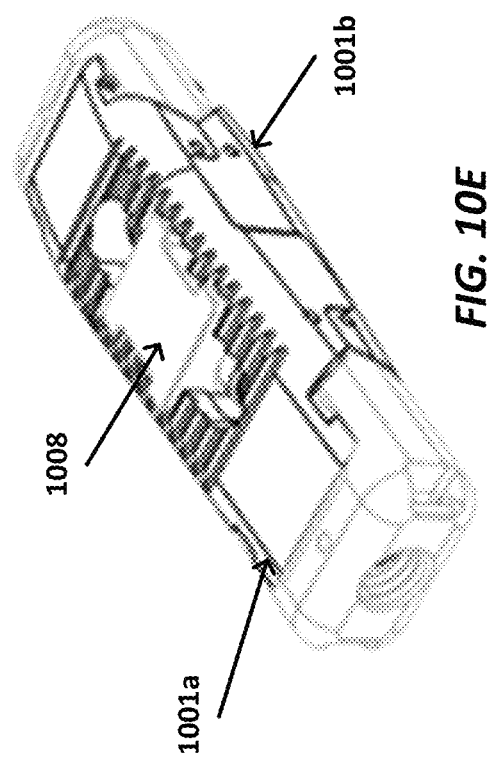
Figure 10H:
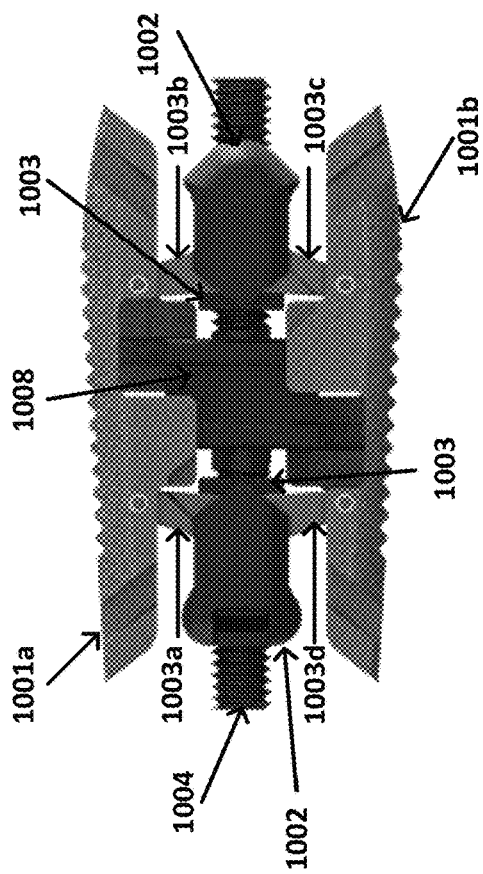
Figure 10G:
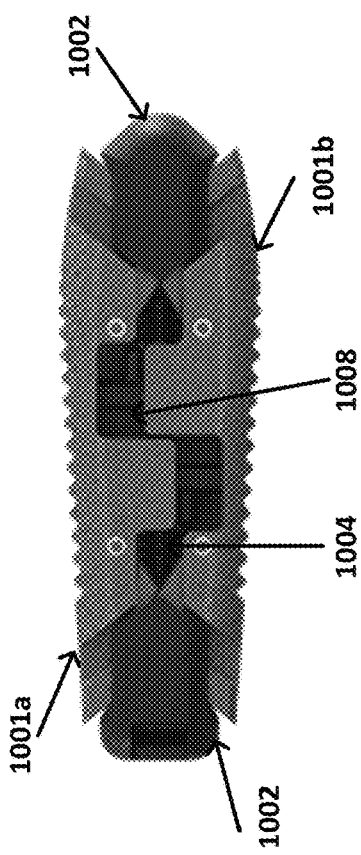

As described herein, the device has a dual stage mechanism (e.g., wedge blocks 1002 and linkage blocks 1003) controlled by rotation of the drive screw 1004. In a first stage, the device expands between the closed and intermediate positions. To accomplish this, the threads of the drive screw 1004 are timed such that only the wedge blocks 1002 are engaged by the drive screw 1004 during the first stage. The threads can be timed such that the wedge blocks 1002 move together and in opposite directions. The drive screw 1004 is therefore configured to rotate and drive the wedge blocks 1002, which moves the upper and lower endplates 1001 of the structural body from a closed position to an intermediate position. FIGS. 10A, 10E, and 10G illustrate the device in the closed position, while FIGS. 10B and 10C illustrate the device in the intermediate position. As shown in FIG. 10A, angled bosses 1005 are included on the upper and/or lower endplates 1001, and angled grooves 1006 are included on the wedge blocks 1002. The angled grooves 1006 can be configured to engage with the angled bosses 1005 to expand the upper and lower endplates 1001 of the structural body as the wedge blocks 1002 translate due to rotation of the drive screw 1004. In other words, the wedge blocks 1002 control expansion in the first stage by physically forcing the endplates 1001 apart. Optionally, the angled bosses/angled grooves can function as a ratchet, e.g., such that the structural body expands (or contracts) in a step-wise manner as the drive screw 1004 is rotated. Once the device reaches the intermediate position (e.g., as shown in FIGS. 10B and 10C), the wedge blocks 1002 disengage with the structural body (e.g., no more contact with the structural body).

In a second stage, the device expands between the intermediate and open positions. To accomplish this, the threads of the drive screw 1004 are timed such that the linkage blocks 1003 are engaged by the drive screw 1004 during the second stage. The threads can be timed such that the linkage blocks 1003 move together and only after initial expansion by the wedge blocks 1002. In other words, the drive screw 1004 can be configured to engage the linkage blocks 1003 at the intermediate position. The drive screw 1004 is therefore configured to rotate and drive the linkage blocks 1003, which further expands the upper and lower endplates 1001 of the structural body from the intermediate position to an open position. FIGS. 10B and 10C illustrate the device in the intermediate position, while FIGS. 10F and 10H illustrates the device in the open position. As shown in FIGS. 10C and 10H, the linkage blocks 1003 include one or more linkages 1003a-1003d (e.g., levers) that are configured to displace the endplates 1001 when the linkage blocks 1003 are engaged by the drive screw 1004. A linkage (e.g., one of linkages 1003a-1003d) is attached between a linkage block (e.g., one of linkage blocks 1003) and an endplate 1001 (e.g., one of endplates 1001). In other words, the linkage blocks 1003 control expansion in the second stage by moving the endplates 1001 with the linkages 1003a-1003d. The dual stage expansion described above (e.g., using both wedge and linkage blocks) allows the device to expand farther than conventional devices. For example, by using the linkage blocks 1003, the device can expand double its initial height, which would be a limiting factor for devices that use only wedge blocks as a drive mechanism. Additionally, the linkages 1003a-1003d experience higher stresses at the attachment to the device at more acute angles of the linkages. To combat this, during the first expansion stage (e.g., when the linkages 1003a-1003d are most acute), the wedge blocks 1002 are bearing the load. Once the expansion has reached its maximum height facilitated by the wedge blocks, the wedge blocks 1002 disengage and the linkage blocks 1003 provide for additional expansion of the device. Although examples are provided for expanding the device, it should be understood that the drive screw 1004 can be rotated in the opposite direction to contract or collapse the device. For example, the linkage blocks 1003 can be used to collapse the device from the open position to the intermediate position, and the wedge blocks 1002 can be used to collapse the devices from the intermediate position to the closed position.

The drive screw 1004 can include a driver hole 1007 at one or both ends of the drive screw 1004 (e.g., as shown in FIGS. 10A and 10C, respectively). The driver hole 1007 can be configured to accept the bit of a driver instrument or tool. This disclosure contemplates that the drive screw 1004 can be operated from either end by providing a driver hole 1007 at both ends (e.g., as shown in FIG. 10C). Additionally, as shown in FIGS. 10A, 10E, 10F, 10G, and 10H, the device can further include an alignment block 1008 configured to guide expansion of the structural body. For example, as shown in FIG. 10H, the alignment block 1008 can includes one or more notches that correspond to vertical grooves in the endplates 1001 to keep the expansion of the structural body in the vertical direction.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An expandable interbody device, comprising:
    a structural body having an upper endplate and a lower endplate, wherein the upper and lower endplates are shaped to nest tightly in a closed position, wherein each of the upper and lower endplates include at least one angled boss;
    at least one wedge block arranged between the upper and lower endplates of the structural body, wherein the at least one wedge block includes at least one angled groove, wherein the at least one wedge block defines a wedge block opening, the wedge block opening defining a plurality of threads;
    at least one linkage block arranged between the upper and lower endplates of the structural body; and
    a drive screw threaded through the wedge block opening of the at least one wedge block and through the at least one linkage block, wherein the drive screw is configured to rotate and engage the threads of the wedge block opening to drive the at least one wedge block such that the at least one angled groove of the wedge block engages the at least one angled boss of the upper and lower endplates to cause the upper and lower endplates of the structural body to expand from the closed position to an intermediate position, and wherein the drive screw is further configured to rotate and drive the at least one linkage block to expand the upper and lower endplates of the structural body from the intermediate position to an open position,
    wherein the at least one wedge block is configured to disengage with the structural body at the intermediate position.

2. The expandable interbody device of claim 1, wherein the at least one linkage block comprises one or more linkages configured to expand the upper and lower endplates of the structural body from the intermediate position to the open position.

3. The expandable interbody device of claim 1, wherein the drive screw is configured to engage the at least one linkage block at the intermediate position.

4. The expandable interbody device of claim 1, further comprising a plurality of wedge blocks arranged between the upper and lower endplates and on opposite sides of the structural body, wherein each of the wedge blocks is threaded in an opposite-handed direction, and wherein the drive screw is configured to rotate and drive the wedge blocks in opposite directions.

5. The expandable interbody device of claim 1, further comprising a plurality of linkage blocks arranged between the upper and lower endplates and on opposite sides of the structural body, wherein each of the linkage blocks is threaded in an opposite-handed direction, and wherein the drive screw is configured to rotate and drive the linkage blocks in opposite directions.

6. The expandable interbody device of claim 1, wherein the drive screw comprises at least one driver hole.

7. The expandable interbody device of claim 6, wherein the drive screw comprises a plurality of driver holes arranged at opposite ends of the drive screw.

8. The expandable interbody device of claim 1, further comprising an alignment block configured to guide expansion of the structural body.

9. The expandable interbody device of claim 1, wherein the drive screw defines at least a first threaded portion, a second threaded portion, and a non-threaded portion disposed axially between the first threaded portion and the second threaded portion.

10. The expandable interbody device of claim 1, wherein the drive screw defines threads, and the threads of the drive screw are timed such that only the at least one wedge block engages the threads of the drive screw when the structural body is expanding from the closed position to the intermediate position.

11. The expandable interbody device of claim 10, wherein the threads of the drive screw are timed such that only the at least one linkage block engages the threads of the drive screw when the structural body is expanding from the intermediate position to the open position.

12. The expandable interbody device of claim 1, wherein the drive screw defines threads, and the threads of the drive screw are timed such that only the at least one linkage block engages the threads of the drive screw when the structural body is expanding from the intermediate position to the open position.

* * * * *